(12) United States Patent
Tong

(10) Patent No.: US 9,399,622 B2
(45) Date of Patent: Jul. 26, 2016

(54) NITROXIDE HYDROXYLAMINE AND PHENYLENEDIAMINE COMBINATIONS AS POLYMERIZATION INHIBITORS FOR ETHYLENICALLY UNSATURATED MONOMER PROCESSES

(71) Applicant: Ecolab USA, Inc., Naperville, IL (US)

(72) Inventor: David Youdong Tong, Houston, TX (US)

(73) Assignee: ECOLAB USA INC., Naperville, IL (US)

( * ) Notice: Subject to any disclaimer, the term of this patent is extended or adjusted under 35 U.S.C. 154(b) by 53 days.

(21) Appl. No.: 14/095,606

(22) Filed: Dec. 3, 2013

(65) Prior Publication Data

US 2015/0152053 A1 Jun. 4, 2015

(51) Int. Cl.
  *C07D 211/00* (2006.01)
  *C07D 211/30* (2006.01)
  *C07D 211/94* (2006.01)
  *C07C 67/62* (2006.01)

(52) U.S. Cl.
  CPC .............. *C07D 211/94* (2013.01); *C07C 67/62* (2013.01)

(58) Field of Classification Search
  None
  See application file for complete search history.

(56) References Cited

U.S. PATENT DOCUMENTS

| | | | |
|---|---|---|---|
| 3,959,358 A | 5/1976 | Jursich | |
| 4,720,566 A | 1/1988 | Martin | |
| 4,797,504 A | 1/1989 | Roling | |
| 4,915,873 A | 4/1990 | Abruscato et al. | |
| 5,258,138 A | 11/1993 | Gatechair et al. | |
| 5,290,888 A | 3/1994 | Gatechair et al. | |
| 5,955,643 A | 9/1999 | Lewis | |
| 6,262,323 B1 | 7/2001 | Elder | |
| 6,300,513 B2 | 10/2001 | Sakamoto et al. | |
| 6,337,426 B1 | 1/2002 | Winter | |
| 6,409,887 B1* | 6/2002 | Pryce et al. | 203/9 |
| 6,518,452 B1 | 2/2003 | Aichinger et al. | |
| 6,525,146 B1 | 2/2003 | Shahid | |
| 6,608,226 B1 | 8/2003 | Reid et al. | |
| 6,627,766 B2 | 9/2003 | Reid et al. | |
| 7,651,635 B1 | 1/2010 | Lewis | |
| 8,691,994 B2* | 4/2014 | Tong | 546/248 |
| 2002/0048820 A1 | 4/2002 | Onishi et al. | |
| 2007/0208204 A1* | 9/2007 | Meyer et al. | 585/4 |
| 2012/0203020 A1 | 8/2012 | Tong | |

FOREIGN PATENT DOCUMENTS

| | | |
|---|---|---|
| CN | 103030590 | 4/2013 |
| EP | 2030963 A2 | 3/2009 |
| JP | 2002234858 A | 8/2002 |
| WO | WO 01/40404 A1 | 6/2001 |

OTHER PUBLICATIONS

International Search Report for PCT/US2014/068154 dated Mar. 23, 2015.

* cited by examiner

*Primary Examiner* — Jared D Barsky
(74) *Attorney, Agent, or Firm* — Eric D. Babych; Brinks Gilson & Lione

(57) ABSTRACT

Polymerization inhibitor compositions are provided. The polymerization inhibitor compositions may include at least one hydroxylamine of a nitroxide and at least one phenylenediamine. Methods of inhibiting the unwanted polymerization of monomers are also provided. The methods include adding the presently disclosed polymerization inhibitor compositions to a fluid containing the monomers. The monomers may be ethylenically unsaturated monomers, such as acrylic acid, methacrylic acid, acrylonitrile, methacrylonitrile, acrolein, methacrolein, acrylate, methacrylate, acrylamide, methacrylamide, vinyl acetate, butadiene, ethylene, propylene, and styrene.

3 Claims, 3 Drawing Sheets

NITROXIDE HYDROXYLAMINE AND PHENYLENEDIAMINE COMBINATIONS AS POLYMERIZATION INHIBITORS FOR ETHYLENICALLY UNSATURATED MONOMER PROCESSES

BACKGROUND

1. Field of the Invention

The present disclosure generally relates to polymerization inhibitor blends and methods of using the same. More particularly, the present disclosure relates to compositions for inhibiting polymerization of monomers comprising at least one hydroxylamine of a nitroxide and at least one phenylenediamine.

2. Description of the Related Art

Premature polymerization of ethylenically unsaturated monomers is a major fouling mechanism in a monomer manufacturing process. In general, two categories of compounds have been developed to prevent premature or unwanted polymerization reactions; inhibitors and retarders. Inhibitors prevent polymerization reactions from occurring and are generally consumed rapidly. Retarders slow down the rate of polymerization reactions but are not as effective as inhibitors. Retarders, however, are usually not consumed as quickly as inhibitors.

Most antipolymerants are considered to be inhibitors. Antipolymerants are generally stable free radicals that are highly efficient in capturing or scavenging carbon-centered radicals through coupling reactions. Most antioxidants are considered to be retarders and they are often efficient hydrogen donors. Thus, they are effective in quenching oxygen-centered radicals through donating hydrogen to the oxygen-centered radicals.

Ethylenically unsaturated monomers are reactive by their nature and tend to polymerize through a radical polymerization mechanism, especially at elevated temperatures and when polymerization initiators are present. Unwanted polymerization reactions often impose operational concerns and may impose serious operational problems when a distillation operation is involved because the elevated temperatures can accelerate polymerization.

The manufacture of ethylenically unsaturated monomers typically comprises three stages: reaction, recovery, and purification. Distillation operations at elevated temperatures are often involved in the recovery and the purification stages. Polymerization of the ethylenically unsaturated monomer during manufacture is generally unwanted because the resulting polymer can precipitate out of the process stream, deposit on the process equipment surfaces, and impair the proper functioning of the equipment. Thus, polymerization inhibitors have conventionally been used when carrying out the monomer manufacturing processes.

Phenolic and phenylenediamine antioxidants, nitroxide stable free radicals, and phenothiazine derivatives are commonly used reagents for polymerization inhibition in the industry. Hydroquinone (HQ), phenothiazine (PTZ), phenylenediamine (PDA), and 4-hydroxy-2,2,6,6-tetramethyl piperidinyl oxy (HTMPO) are examples of some of the most commonly used polymerization inhibitors in the industry. However, a conventional inhibitor treatment often does not provide adequate protection from the polymerization-induced fouling. Furthermore, use of the conventional inhibitors often poses logistic, economic, and safety concerns.

BRIEF SUMMARY

Compositions are provided for inhibiting polymerization of monomers. In one aspect, a composition for inhibiting polymerization of monomers comprises at least one hydroxylamine of a nitroxide and at least one phenylenediamine.

Methods of inhibiting the polymerization of monomers are also provided herein. In one aspect, a method of inhibiting polymerization of a monomer comprises providing a fluid comprising an ethylenically unsaturated monomer and adding an effective amount of a polymerization inhibitor composition to the fluid. The polymerization inhibitor composition comprises an effective amount of at least one hydroxylamine of a nitroxide and an effective amount of at least one phenylenediamine. Addition of the polymerization inhibitor composition to the fluid will thereby inhibit polymerization of the ethylenically unsaturated monomer.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE SEVERAL VIEWS OF THE DRAWINGS

A detailed description of the invention is hereafter described with specific reference being made to the drawings in which.

DETAILED DESCRIPTION

Figure 1:
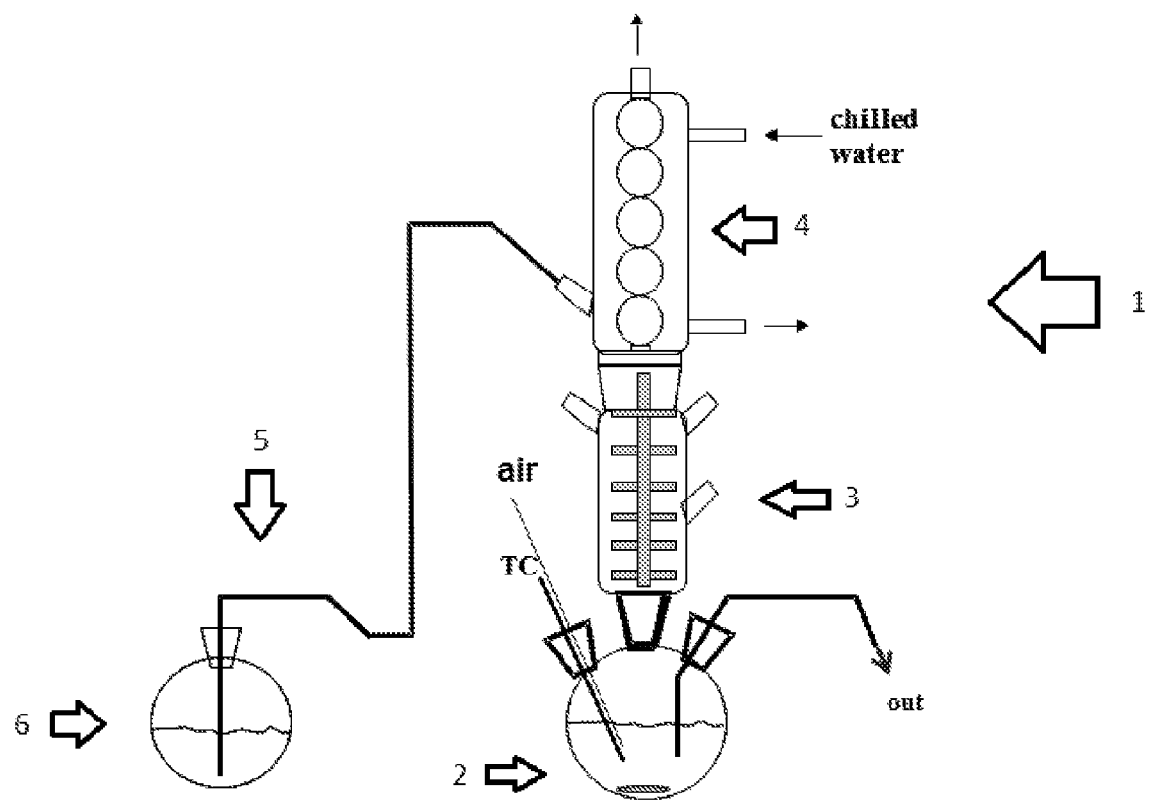
FIG. 1 shows laboratory equipment used to carry out an experimental analysis of the presently disclosed polymerization inhibitor compositions.

Various embodiments of the present disclosure are described below. The relationship and functioning of the various elements of the embodiments may better be understood by reference to the following detailed description. However, embodiments are not limited to those explicitly described herein and it should be understood that in certain instances, details may have been omitted that are not necessary for an understanding of the embodiments disclosed herein, such as conventional assembly and synthesis.

The present disclosure relates to polymerization inhibitor blends and methods of inhibiting the polymerization of ethylenically unsaturated monomers. A polymerization inhibitor blend/composition according to the present disclosure may be a blend/composition comprising multiple components. In one aspect, the polymerization inhibitor blend/composition comprises at least one hydroxylamine of a nitroxide and at least one phenylenediamine. Any of the presently disclosed polymerization inhibitor blends/compositions are effective in scavenging the free radicals participating in the initiation and propagation of a polymerization reaction.

In accordance with the present disclosure, the hydroxylamine of a nitroxide may comprise either of the following general chemical structures:

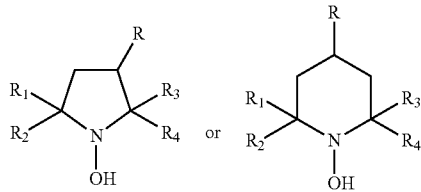

wherein each $R_1$, $R_2$, $R_3$ and $R_4$ is independently selected from any alkyl group. For example, each $R_1$, $R_2$, $R_3$, or $R_4$ may be independently selected from the group consisting of any $C_1$-$C_8$ alkyl group. Thus, in some aspects, each $R_1$, $R_2$, $R_3$ or $R_4$ may be independently selected from the group consisting of methyl, ethyl, propyl, butyl, pentyl, hexyl, haptanyl, and octyl. R is independently selected from the group consisting of hydrogen, oxygen, alkyl, hydroxyl, alkoxyl, amino, amido and carboxylate.

The following are general structures of hydroxylamines of the six member ring nitroxides that can be used in accordance with the present disclosure:

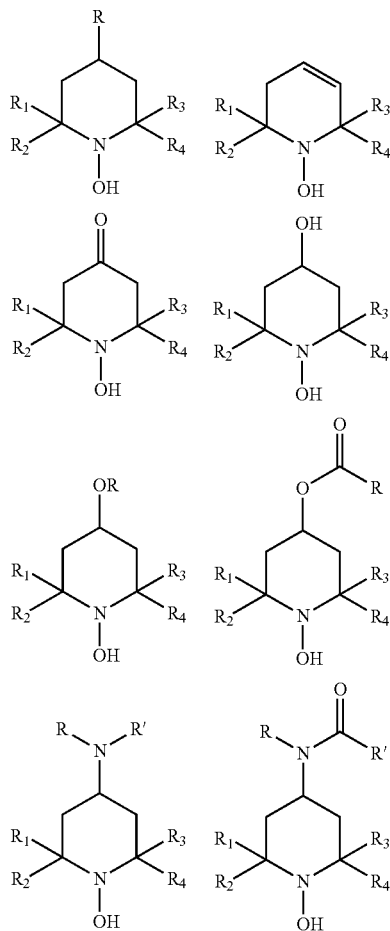

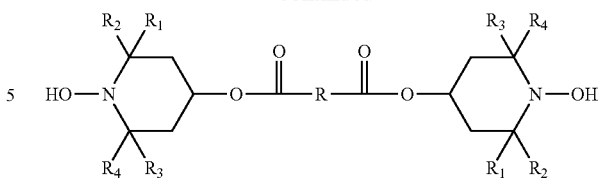

wherein each $R_1$, $R_2$, $R_3$ and $R_4$ is independently selected from any alkyl group. For example, each $R_1$, $R_2$, $R_3$, or $R_4$ may be independently selected from the group consisting of any $C_1$-$C_8$ alkyl group. Thus, in some aspects, each $R_1$, $R_2$, $R_3$ or $R_4$ may be independently selected from the group consisting of methyl, ethyl, propyl, butyl, pentyl, hexyl, haptanyl, and octyl. R and R' are independently selected from the group consisting of hydrogenalkyl and aryl.

Therefore, in certain aspects of the present disclosure, the hydroxylamine of a nitroxide may be selected from the group consisting of 4-hydroxy-2,2,6,6-tetramethyl piperidinol, 4-oxo-2,2,6,6-tetramethyl piperidinol, 4-methoxy-2,2,6,6-tetramethyl piperidinol, 4-acetate-2,2,6,6-tetramethyl piperidinol, 4-amino-2,2,6,6-tetramethyl piperidinol, 4-acetamido-2,2,6,6-tetramethyl piperidinol, 1,2,3,6-tetrahydro-2,2,6,6-tetramethyl piperidinol, bis(2,2,6,6-tetramethylpiperidinol) sebacate and any combination thereof. In one particular aspect, the hydroxylamine of a nitroxide is 4-hydroxy-2,2,6,6-tetramethyl piperidinol.

None of the presently disclosed hydroxylamines of nitroxides should be confused with the corresponding nitroxides. The presently disclosed hydroxylamines of nitroxides have benefits over their corresponding nitroxides, such as the capability to provide additional polymerization inhibition, as will be more fully explained below. A general synthetic route to produce a hydroxylamine of a nitroxide is to reduce its corresponding nitroxide with a reducing reagent as follows:

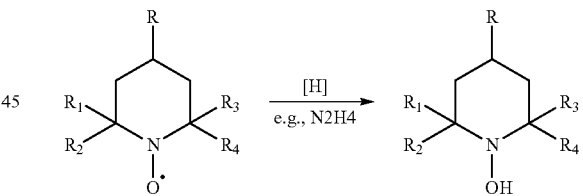

A hydroxylamine of a nitroxide has the potential to provide additional polymerization inhibition as compared to the corresponding nitroxide when carbon-centered and oxygen-centered radical initiators are present. This is explained as follows:

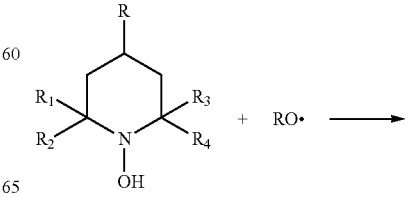

-continued

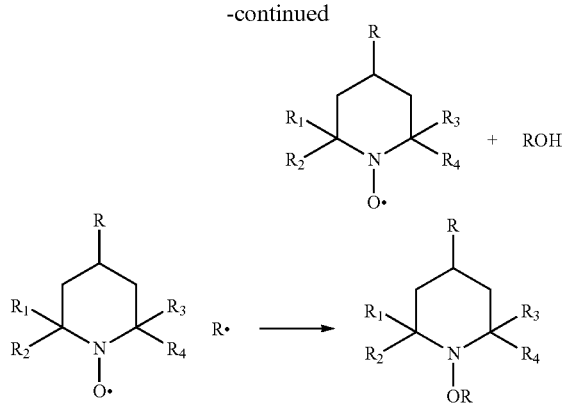

The hydroxylamine of a nitroxide is an excellent hydrogen donor due to its weak NO—H bond in the compound, and thus it is an efficient antioxidant. As an antioxidant, the hydroxylamine of a nitroxide easily reacts with oxygen-centered radicals, such as peroxide radicals, while it's converted to its corresponding nitroxide. Nitroxides are generally known as the most effective inhibitors because of their superior inhibiting capabilities through scavenging carbon-centered free radicals at a nearly diffusion-controlled rate. This rate is several orders of magnitude faster than phenolic compounds. However, their kinetic superiority is not always advantageous. For instance, it may lose its superiority when oxygen-centered radicals are present as the predominant free radicals. Another issue of concern with a nitroxide is its consumption through non-inhibition and unwanted reactions with process stream components or other inhibitor additives. As a result, high nitroxide inhibitor dosages are often required for a given inhibition efficacy, thereby making their use economically unattractive or even infeasible.

In essence, each hydroxylamine of a nitroxide is equivalent to one hydrogen donor plus one nitroxide antipolymerant when oxygen-centered radicals and carbon-centered radicals are both present, which is an attractive incentive offered by the hydroxylamines of nitroxides. That is, one hydroxylamine of a nitroxide is able to eliminate one oxygen-centered radical and one carbon-centered radical whereas a nitroxide is only capable to eliminate a carbon-centered radical.

The phenylenediamine of the present disclosure comprises the following general structure:

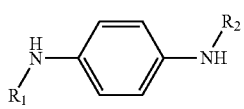

wherein $R_1$ or $R_2$ may be independently selected from the group consisting of hydrogen, alkyl, alkylaryl, aryl, arylalkyl, hydroxyl-containing alkyl groups, ethoxylate-containing alkyl groups, and amino-containing alkyl groups.

Therefore, in certain aspects of the present disclosure, the phenylenediamine is selected from the group consisting of 1,2-phenylenediamine, 1,4-phenylenediamine, N,N'-di-methyl-p-phenylenediamine, N,N'-di-sec-butyl-1,4-phenylenediamine, N,N'-di-1,4-dimethylpentyl-1,4-phenylenediamine, N,N'-di-acetyl-1,4-phenylenediamine, N-tert-butyl-N'-phenyl-1,4-phenylenediamine, N,N'-di-phenyl-1,4-phenylenediamine, and any combination thereof. In one particular aspect, the phenylenediamine is N,N'-di-sec-butyl-1,4-phenylenediamine or N,N'-di-1,4-dimethylpentyl-1,4-phenylenediamine.

Any aspect of the presently disclosed polymerization inhibitor may comprise a combination of two or more components, such as at least one hydroxylamine of a nitroxide and at least one phenylenediamine. The polymerization inhibitor may include any amount of each component. For example, in some aspects, it may include a greater amount of hydroxylamine of a nitroxide than phenylenediamine. In another aspect, it may include a greater amount of phenylenediamine than hydroxylamine of a nitroxide. In additional aspects, it may include equal amounts of the hydroxylamine of a nitroxide and phenylenediamine. Therefore, in some aspects, the ratio of the at least one hydroxylamine of a nitroxide to the at least one phenylenediamine may be from about 10:1 to about 1:10 by weight, or from about 5:1 to about 1:5, or about 1:1.

The presently disclosed polymerization inhibitor compositions are a significant improvement over conventional polymerization inhibitor compositions. For example, the polymerization inhibitor compositions of the present disclosure have much improved efficacy, safety/handling, environmental impact, dosage requirements, and treatment costs. Many, if not all, of these improvements are based in part on synergy that the present inventors have unexpectedly discovered between various components of the presently disclosed polymerization inhibitor compositions.

In accordance with the present disclosure, various methods are disclosed for inhibiting the polymerization of monomers. In one aspect, a method is provided for inhibiting the polymerization of ethylenically unsaturated monomers. Ethylenically unsaturated monomers are very well-known in the art and all ethylenically unsaturated monomers are intended to be covered by the present disclosure. That is, the presently disclosed polymerization inhibitor compositions can inhibit the polymerization of any ethylenically unsaturated monomer.

In some aspects of this disclosure, the ethylenically unsaturated monomer is selected from the group consisting of acrylic acid, methacrylic acid, acrylonitrile, methacrylonitrile, acrolein, methacrolein, acrylate, methacrylate, acrylamide, methacrylamide, vinyl acetate, butadiene, ethylene, propylene, and styrene.

In accordance with one aspect of the present disclosure, a method of inhibiting polymerization of an ethylenically unsaturated monomer is disclosed. Again, the ethylenically unsaturated monomer can be any ethylenically unsaturated monomer. The method comprises a step of providing a fluid comprising an ethylenically unsaturated monomer. The fluid is not limited to any particular fluid and can be any fluid that is present in a monomer manufacturing process. The fluid may be the process stream comprising the monomers to which a polymerization inhibitor composition is added.

An effective amount of one or more of the presently disclosed polymerization inhibitor compositions is then added to the fluid. For example, an effective amount of a composition comprising at least one hydroxylamine of a nitroxide and at least one phenylenediamine may be added to the fluid.

The hydroxylamine of a nitroxide and/or phenylenediamine, and/or any other components of the presently disclosed polymerization inhibitor composition, may be added manually or automatically to the fluid. They may also be added continuously and/or intermittently. Automatic addition may be accomplished through the use of chemical injection pumps. The chemical injection pumps may be programmed to add particular amounts of the polymerization inhibitor composition, or any components thereof, at certain time intervals to the fluid. In alternate aspects, the chemical injection pumps can be manually controlled to add particular amounts of the polymerization inhibitor composition, or any components thereof, to the fluid. Moreover, the phenylenediamine and hydroxylamine of a nitroxide, or any other components of the polymerization inhibitor composition, may be added together in a single solution to the fluid or they may be added separately to the fluid. Addition of the presently disclosed polymerization inhibitor compositions to the fluid containing the ethylenically unsaturated monomer will thereby inhibit polymerization of the ethylenically unsaturated monomer.

The effective amount of the at least one hydroxylamine of a nitroxide can be any amount that will effectively inhibit polymerization of the monomers. For example, the effective amount of the hydroxylamine of a nitroxide may be from about 1 ppm to about 2,000 ppm, based on the weight of the monomers. In one aspect, the effective amount may be from about 5 ppm to about 500 ppm. In another aspect, the effective amount of the hydroxylamine of a nitroxide may be from about 10 ppm to about 200 ppm.

The effective amount of the at least one phenylenediamine can be any amount that will effectively inhibit polymerization of the monomers. For example, the effective amount of the phenylenediamine may be from about 1 ppm to about 2,000 ppm, based on the weight of the monomers. In one aspect, the effective amount may be from about 5 ppm to about 500 ppm. In another aspect, the effective amount of the phenylenediamine may be from about 10 ppm to about 200 ppm.

EXAMPLES

Performance of polymerization inhibitor compositions was evaluated using a laboratory scale continuous flow distillation column (see FIG. 1). In this laboratory setup, the column (1) included a three-neck flask (2) representing the column sump and boiler, an insertion assembly (3) with perforated metal plates representing the distillation column tray section, and a condenser (4) representing the overhead condenser to provide distillation reflux. A feed pump (5) provided the column feed, and an outlet purge pump maintained the liquid level in the sump. Heating was provided via a heating mantle to the flask contents at a temperature between about 85° C. and about 95° C. This apparatus simulates the operation and fouling environment in a typical acrylate process distillation operation.

Commercial grade methyl methacrylate (MMA) inhibited with 10-35 ppm mono methyl ether hydroquinone (MEHQ) was obtained. Uninhibited methyl methacrylate was obtained by removing the MEHQ with inhibitor remover. Benzoyl peroxide (BPO) was employed as the polymerization initiator for the experiments.

A polymerization inhibitor was dosed into the uninhibited monomer (MMA) solution along with BPO. A portion of the resulting solution was poured into the three-neck flask and heat was applied. The remaining portion of the polymerization inhibitor/uninhibited monomer solution was poured into the feed tank (6). While carrying out the experiment, the portion of the polymerization inhibitor/uninhibited monomer solution in the feed tank is pumped into the distillation column from the feed tank while the contents in the three-neck flask are pumped out continuously.

In a first set of experiments, polymerization inhibitor compositions according to the present disclosure were compared to conventional polymerization inhibitors. In the first trial, 100 ppm phenothiazine (PTZ) was dosed into the uninhibited monomer solution. In a second trial, 100 ppm 4-hydroxy-2,2,6,6-tetramethyl piperidinyl oxy (HTMPO) was dosed into the uninhibited monomer solution. In a third trial, 100 ppm hydroquinone (HQ) was dosed into the uninhibited monomer solution and in a fourth trial, about 18 ppm N,N'-di-sec-butyl-1,4-phenylenediamine and about 18 ppm 4-hydroxy-2,2,6,6-tetramethyl piperidinol (HTMPOH) was dosed into the uninhibited monomer solution. Each trial was handled according to the experimental procedures described above, e.g. pouring a portion of the solution into the three-neck flask, pouring the remainder into the feed tank, pumping the solution from the feed tank into the distillation column, etc.

For a typical performance test, the polymer concentration in the sump increased with time as a result of polymer formation. An effective polymerization inhibitor composition would be expected to reduce polymer formation in the distillation column and thus slow down the concentration rise of polymer in the sump.

Figure 2:
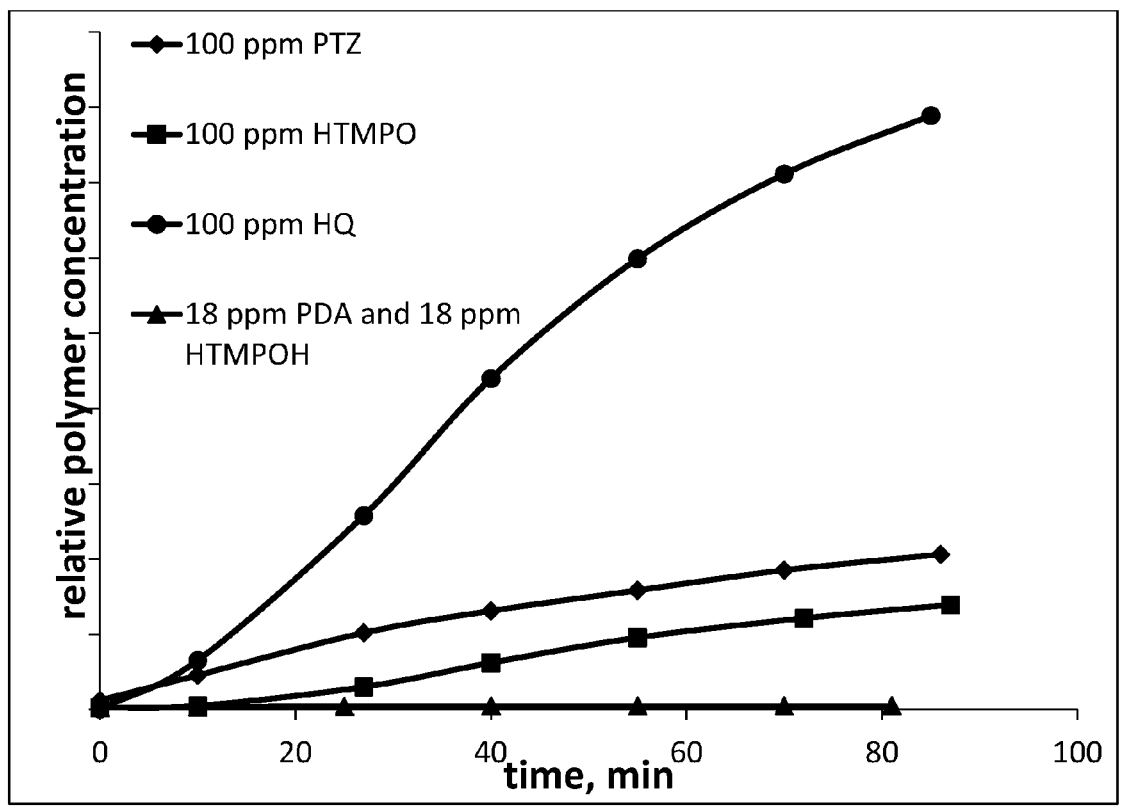
FIG. 2 is a graphical analysis comparing aspects of the presently disclosed polymerization inhibitor compositions with conventional inhibitors.

As can be seen in FIG. 2, the polymerization inhibitor according to the present disclosure outperformed all conventional polymerization inhibitors by producing the lowest relative polymer concentration.

The same experimental steps previously described were used in a second set of experiments to show the synergistic effect of an aspect of the polymerization inhibitor composition of the present disclosure. In one trial, about 10 ppm N,N'-di-sec-butyl-1,4-phenylenediamine was added to the uninhibited monomer solution. In a second trial, about 10 ppm HTMPOH was added to the uninhibited monomer solution and in a third trial, about 10 ppm N,N'-di-sec-butyl-1,4-phenylenediamine plus about 10 ppm HTMPOH was added into the uninhibited monomer solution.

Figure 3:
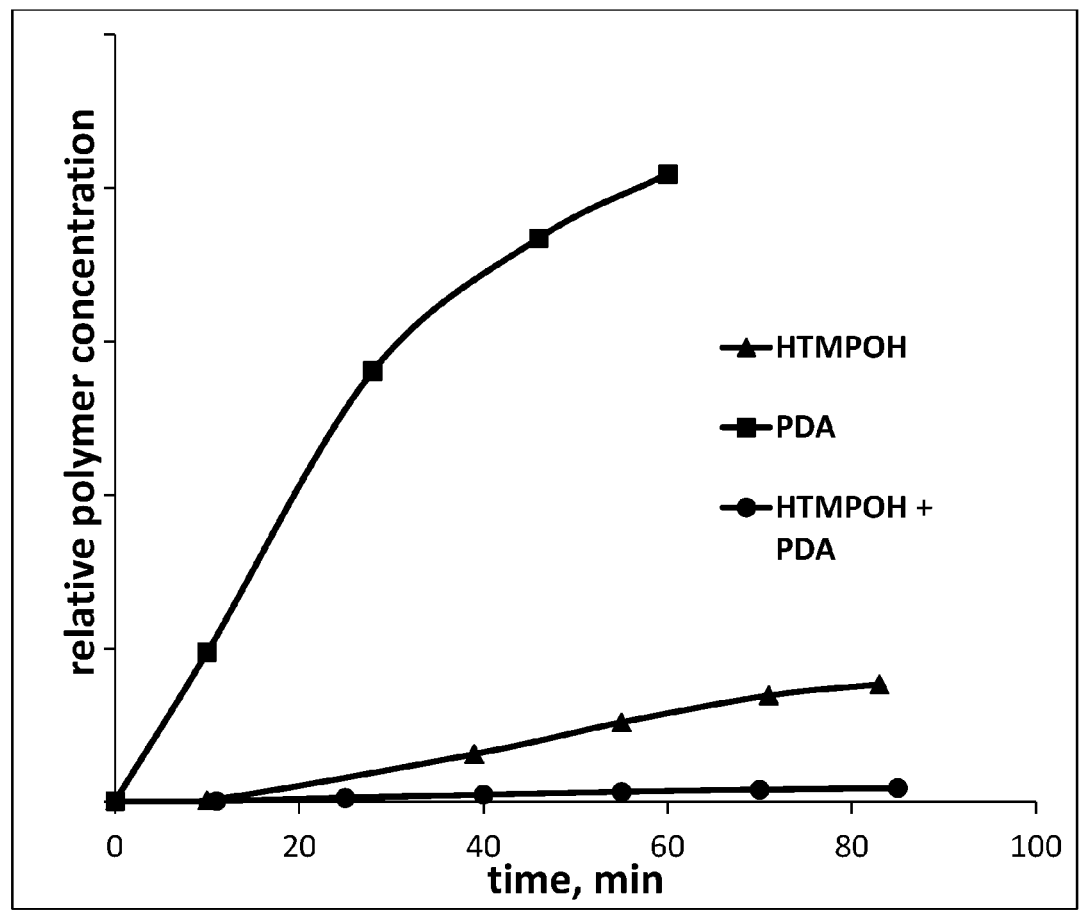
FIG. 3 is a graphical analysis showing synergism between two components of the presently disclosed polymerization inhibitor compositions.

The results of these trials are shown in FIG. 3, which clearly indicate a strong synergism between HTMPOH and N,N'-di-sec-butyl-1,4-phenylenediamine. This synergism can be expected to be present in any aspect of the presently disclosed polymerization inhibitor compositions.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a polymerization inhibitor" is intended to include "at least one polymerization inhibitor" or "one or more polymerization inhibitors."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A method of inhibiting polymerization of methyl methacrylate comprising:
   providing a fluid comprising methyl methacrylate;
   adding an effective amount of a polymerization inhibitor composition to the fluid, wherein the polymerization inhibitor composition comprises an effective amount of 4-hydroxy-2,2,6,6-tetramethyl piperidinol and an effective amount of N,N'-di-1,4-dimethylpentyl-1,4-phenylenediamine; and
   inhibiting polymerization of the methyl methacrylate.

2. The method of claim 1, wherein the effective amount of the 4-hydroxy-2,2,6,6-tetramethyl piperidinol and the effective amount of the N,N'-di-1,4-dimethylpentyl-1,4-phenylenediamine is from about 1 ppm to about 2,000 ppm by weight of methyl methacrylate.

3. The method of claim 1, wherein the polymerization inhibitor composition is added continuously or intermittently to the fluid.

* * * * *